(12) United States Patent
Bracco et al.

(10) Patent No.: US 6,852,509 B1
(45) Date of Patent: *Feb. 8, 2005

(54) ANTI-P53 SINGLE-CHAIN ANTIBODY FRAGMENTS AND THEIR USES

(76) Inventors: Laurent Bracco, 30 rue Deparcieux, 75014 Paris (FR); Laurent Debussche, 112, Avenue Jean Jaures, 91200 Athis Mons (FR); Claude Caron De Fromentel, 22 route de Collonges, Saint Cyr au Mont d'Or, 69450 (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,181
(22) PCT Filed: Oct. 27, 1997
(86) PCT No.: PCT/FR97/01921
  § 371 (c)(1),
  (2), (4) Date: Apr. 26, 1999
(87) PCT Pub. No.: WO98/18825
  PCT Pub. Date: May 7, 1998

(30) Foreign Application Priority Data

Oct. 29, 1996 (FR) .......................................... 96 13176

(51) Int. Cl.[7] ........................... C12P 21/06; C12N 5/00; C12N 15/63; C07K 16/00; C07H 21/02
(52) U.S. Cl. ................... 435/69.1; 435/320.1; 435/325; 435/455; 530/350; 530/387.1; 530/389.1; 530/389.2; 536/23.1; 536/23.5
(58) Field of Search ........................... 435/69.1, 320.1, 435/325, 455; 536/23.1, 23.5; 530/350, 387.1, 389.1, 389.2, 388.1, 388.15, 388.2; 514/44

(56) References Cited

FOREIGN PATENT DOCUMENTS

| WO | WO 94/12202 | 6/1994 |
| WO | WO 96/30512 | 10/1996 |
| WO | WO 97/04092 | 2/1997 |

OTHER PUBLICATIONS

Herbert et al. The Dictionary of Immunology, Academic Press, 4th edition, 1995).*
Greenspan et al, Definig epitopes: It's not easy as it semms. Nature Biotechnology 7:936–937, 1999.*
Legros et al Mutations in p53 produce a common conformational effect that can be detected with a panel of monoclonal antibodies directed toward the central part of the p53 protein. Oncogene 9:3689–3694, 1994.*
Caron de Fromentel et al Restoration of transcriptional activity of p53 mutants in human tumour cells by intracellular expression of anti–p53 single chain Fv fragments. Oncogene 18(2):551–7, 1999.*
Rosenberg et al., Gene therapist, heal thyself, 2000, SCIENCE, vol. 287 p. 1751.*
Verma, Gene therapy beyond 2000, 2000, Molecular Therapy, vol. 1 No. 6 p. 493.*
Friedmann, Principles for human gene therapy studies, 2000, SCIENCE, vol. 287, pp. 2163–2164.*
Anderson, Human gene therapy, 1998, NATURE, vol. 392, pp. 25–30.*
Verma et al., Gene therapy–promises, problems and prospects, 1997, Nature, vol. 389, pp. 239–242.*
Jannot et al., Characterization of scFv–421, a single–chain antibody targeted to p53, 1997, Biochemical and Biophysical Research Communications, vol. 230, pp. 242–246.*
Hupp et al., Strategies for manipulating the p53 pathway in the treatment of human cancer, 2000, Biochemistry Journal, vol. 352 pp. 1–17.*
Mastrangelo et al., Gene therapy for human cancer: An essay for clinicians, 1996, Seminars in Oncology, vol. 23 No. 1 pp. 4–21.*
Gomez–Navarro et al., Gene therapy for cancer, 1999, European Journal of Cancer, vol. 35 No. 6 pp. 867–885.*
Kelloff et al., Cancer chemoprevention: progress and promise, 1999, European Journal of Cancer, vol. 35 No. 14 pp. 2031–2038.*
Varmus, Gene therapy: Not ready for prime time, 1996, Nature Medicine, vol. 2 No. 1 pp. 7–8.*
Abarzua et al., Microinjection of Monoclonal Antibody PAb421 Into Human SW480 Colorectal Carcinoma Cells Restores the Trascription Activation Function To Mutant p53, Cancer Research 55, 3490–3494 (1995).
Hupp et al., Regulation of the Specific DNA Binding Function of p53, Cell, 71, 875–886 (1992).
Halazonetis et al., Wild–type p53 adopts a 'mutant'–like conformation when bound to DNA, The EMBO Journal 12(3), 1021–1028 (1993).
Jannot et al., Characterization of scFv–421, a Single–Chain Antibody Targeted to p53, Biochemical & Biophysical Research Comm., 230, 242–246 (1997).

* cited by examiner

*Primary Examiner*—Jeffrey Fredman
*Assistant Examiner*—Sumesh Kaushal
(74) *Attorney, Agent, or Firm*—Wiley Rein & Fielding, LLP

(57) ABSTRACT

The invention concerns single-chain antibodies directed against the p53 protein, capable of being expressed in tumoral cells, capable of restoring a DNA binding in vitro and a transcription activator function in vivo. The invention also concerns nucleic acids coding for these molecules, the vectors containing them and their uses.

5 Claims, 9 Drawing Sheets

SECONDARY SCREENINGS

Figure 2:
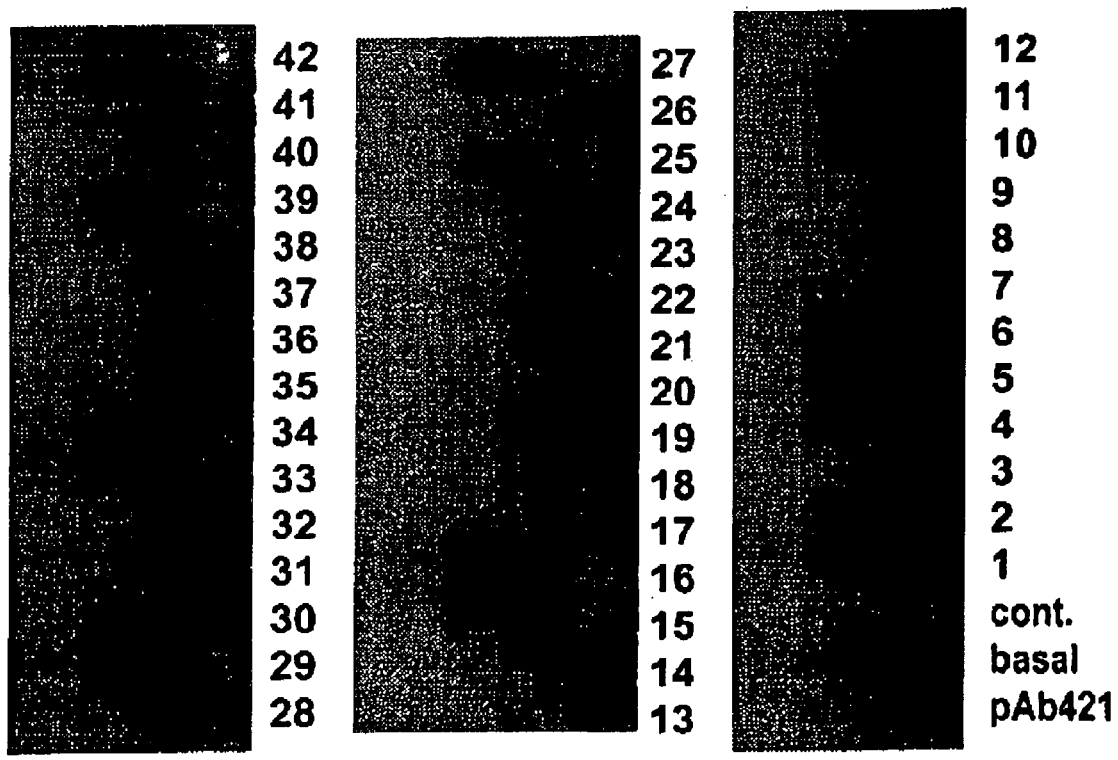

---
→ Mapping N-terminal/central/C-terminal
---

ELISA 1-320/73-320

| | | | | |
|---|---|---|---|---|
| WT | − | + | + | + |
| 1-320 | − | − | − | + |
| 73-320 | − | − | − | + |
| | lost | C-ter | N-ter | central |
| | 162 | 33 | 115 | 7 |

---
→ Selection of N-terminal antibodies
---

ELISA WT + displacement by peptides 1-40/34-73

77 antibodies displaced by 1-40

27 antibodies displaced by 34-73

11 antibodies not displaced

---
→ Elimination of the IgMs
---

Isotyping

Figure 1

Basal
+HR231
+pAb421
+11D3
+ScFv421 (2)
+ScFv421 (5)
+ScFv421 (10)
+ScFvD3M (2)
+ScFvD3M (5)
+ScFvD3M (10)
+ScFvY28 (2)
+ScFvY28 (5)
+ScFvY28 (10)

SEQUENCE LISTING

```
<160> NUMBER OF SEQ ID NOS: 4

<210> SEQ ID NO 1
<211> LENGTH: 729
<212> TYPE: DNA
<213> ORGANISM: Mus musculus
<220> FEATURE:
<221> NAME/KEY: CDS
<222> LOCATION: (1)..(729)

<400> SEQUENCE: 1 cag gtg cag ctg cag cag tct ggg gca gag ctt gtg agg tca ggg gcc      48
Gln Val Gln Leu Gln Gln Ser Gly Ala Glu Leu Val Arg Ser Gly Ala
  1               5                  10                  15 tca gtc aag ttg tcc tgc aca gct tct ggc ttc aac att aaa gac tac      96
Ser Val Lys Leu Ser Cys Thr Ala Ser Gly Phe Asn Ile Lys Asp Tyr
```

```
                       20                  25                    30
tat atg cac tgg gtg aag cag agg cct gaa cag ggc ctg gag tgg att       144
Tyr Met His Trp Val Lys Gln Arg Pro Glu Gln Gly Leu Glu Trp Ile
            35                  40                  45 gga tgg att gat cct gag aat ggt gat act gaa tat gcc ccg aag ttc       192
Gly Trp Ile Asp Pro Glu Asn Gly Asp Thr Glu Tyr Ala Pro Lys Phe
 50                  55                  60 cag ggc aag gcc act atg act gca gac aca tcc tcc aat aca gcc tac       240
Gln Gly Lys Ala Thr Met Thr Ala Asp Thr Ser Ser Asn Thr Ala Tyr
 65                  70                  75                  80 ctg cag ctc agc agc ctg gca tct gag gac act gcc gtc tat tat tgt       288
Leu Gln Leu Ser Ser Leu Ala Ser Glu Asp Thr Ala Val Tyr Tyr Cys
                 85                  90                  95 aat ttt tac ggg gat gct ttg gac tat tgg ggc caa ggg acc acg gtc       336
Asn Phe Tyr Gly Asp Ala Leu Asp Tyr Trp Gly Gln Gly Thr Thr Val
             100                 105                 110 acc gtc tcc tca ggt gga ggc ggt tca ggc gga ggt ggc tct ggc ggt       384
Thr Val Ser Ser Gly Gly Gly Gly Ser Gly Gly Gly Gly Ser Gly Gly
         115                 120                 125 ggc gga tcg gat gtt ttg atg acc caa act cca ctc act ttg tcg gtt       432
Gly Gly Ser Asp Val Leu Met Thr Gln Thr Pro Leu Thr Leu Ser Val
     130                 135                 140 acc att gga caa cca gcc tcc atc tct tgc aag tca agt cag agc ctc       480
Thr Ile Gly Gln Pro Ala Ser Ile Ser Cys Lys Ser Ser Gln Ser Leu
145                 150                 155                 160 ttg gat agt gat gga aag aca tat ttg aat tgg ttg tta cag agg cca       528
Leu Asp Ser Asp Gly Lys Thr Tyr Leu Asn Trp Leu Leu Gln Arg Pro
                 165                 170                 175 ggc cag tct cca aag cgc cta atc tat ctg gtg tct aaa ctg gac tct       576
Gly Gln Ser Pro Lys Arg Leu Ile Tyr Leu Val Ser Lys Leu Asp Ser
             180                 185                 190 gga gtc cct gac agg ttc act ggc agt gga tca ggg aca gat ttc aca       624
Gly Val Pro Asp Arg Phe Thr Gly Ser Gly Ser Gly Thr Asp Phe Thr
         195                 200                 205 ctg aaa atc aac aga gtg gag gct gag gat ttg gga gtt tat tat tgc       672
Leu Lys Ile Asn Arg Val Glu Ala Glu Asp Leu Gly Val Tyr Tyr Cys
     210                 215                 220 tgg caa ggt aca cat tct ccg ctc acg ttc ggt gct ggc acc aag ctg       720
Trp Gln Gly Thr His Ser Pro Leu Thr Phe Gly Ala Gly Thr Lys Leu
225                 230                 235                 240 gaa atc aaa                                                           729
Glu Ile Lys <210> SEQ ID NO 2
<211> LENGTH: 243
<212> TYPE: PRT
<213> ORGANISM: Mus musculus

<400> SEQUENCE: 2

Gln Val Gln Leu Gln Gln Ser Gly Ala Glu Leu Val Arg Ser Gly Ala
  1               5                  10                  15

Ser Val Lys Leu Ser Cys Thr Ala Ser Gly Phe Asn Ile Lys Asp Tyr
                 20                  25                  30

Tyr Met His Trp Val Lys Gln Arg Pro Glu Gln Gly Leu Glu Trp Ile
             35                  40                  45

Gly Trp Ile Asp Pro Glu Asn Gly Asp Thr Glu Tyr Ala Pro Lys Phe
         50                  55                  60

Gln Gly Lys Ala Thr Met Thr Ala Asp Thr Ser Ser Asn Thr Ala Tyr
 65                  70                  75                  80
```

```
Leu Gln Leu Ser Ser Leu Ala Ser Glu Asp Thr Ala Val Tyr Tyr Cys
                85                  90                  95

Asn Phe Tyr Gly Asp Ala Leu Asp Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Asp Val Leu Met Thr Gln Thr Pro Leu Thr Leu Ser Val
    130                 135                 140

Thr Ile Gly Gln Pro Ala Ser Ile Ser Cys Lys Ser Gln Ser Leu
145                 150                 155                 160

Leu Asp Ser Asp Gly Lys Thr Tyr Leu Asn Trp Leu Leu Gln Arg Pro
                165                 170                 175

Gly Gln Ser Pro Lys Arg Leu Ile Tyr Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Lys Ile Asn Arg Val Glu Ala Glu Asp Leu Gly Val Tyr Tyr Cys
    210                 215                 220

Trp Gln Gly Thr His Ser Pro Leu Thr Phe Gly Ala Gly Thr Lys Leu
225                 230                 235                 240

Glu Ile Lys

<210> SEQ ID NO 3
<211> LENGTH: 747
<212> TYPE: DNA
<213> ORGANISM: Mus musculus
<220> FEATURE:
<221> NAME/KEY: CDS
<222> LOCATION: (1)..(747)

<400> SEQUENCE: 3 cag gtc aag ctg cag gag tca ggg gca gaa ctt gtg agg tca ggg gcc      48
Gln Val Lys Leu Gln Glu Ser Gly Ala Glu Leu Val Arg Ser Gly Ala
 1               5                  10                  15 tca gtc aat ttg tcc tgc aca gct tct ggc ttc aac att aaa gac tac      96
Ser Val Asn Leu Ser Cys Thr Ala Ser Gly Phe Asn Ile Lys Asp Tyr
                20                  25                  30 tat atg cac tgg gtg aaa cag agg cct gaa gag ggc ctg gag tgg att     144
Tyr Met His Trp Val Lys Gln Arg Pro Glu Glu Gly Leu Glu Trp Ile
            35                  40                  45 gga tat att gat cct gag agt ggt gaa act gaa tat gcc ccg aac ttc     192
Gly Tyr Ile Asp Pro Glu Ser Gly Glu Thr Glu Tyr Ala Pro Asn Phe
    50                  55                  60 cag ggc aag gcc act gtg act gca gac aca tcc tcc aac aca gcc tac     240
Gln Gly Lys Ala Thr Val Thr Ala Asp Thr Ser Ser Asn Thr Ala Tyr
 65                  70                  75                  80 ctg cac ctc agc agc ctg aca tct gag gac aca acc gtc tat tac tgt     288
Leu His Leu Ser Ser Leu Thr Ser Glu Asp Thr Thr Val Tyr Tyr Cys
                85                  90                  95 aat gca gtc atc tac tat gaa tac gac ggc tat gct ttg gac tac tgg     336
Asn Ala Val Ile Tyr Tyr Glu Tyr Asp Gly Tyr Ala Leu Asp Tyr Trp
            100                 105                 110 ggc caa ggg acc acg gtc acc gtc tcc tca ggt gga ggc ggt tca ggc     384
Gly Gln Gly Thr Thr Val Thr Val Ser Ser Gly Gly Gly Gly Ser Gly
    115                 120                 125 gga ggt ggc tct ggc ggt ggc gga tcg gac att gag ctc acc cag tct     432
Gly Gly Ser Gly Gly Gly Gly Ser Asp Ile Glu Leu Thr Gln Ser
    130                 135                 140
```

```
cca tct tcc ctg gct gtg tca gca gga gag aag gtc gct atg agc tgc         480
Pro Ser Ser Leu Ala Val Ser Ala Gly Glu Lys Val Ala Met Ser Cys
145                 150                 155                 160 aaa tcc agt cag agt ctg ttc aac agt aga acc cga aag aat tac ttg         528
Lys Ser Ser Gln Ser Leu Phe Asn Ser Arg Thr Arg Lys Asn Tyr Leu
                165                 170                 175 gct tgg tat cag cag aaa cca ggg cag tct cct aaa gtg ctg atc tac         576
Ala Trp Tyr Gln Gln Lys Pro Gly Gln Ser Pro Lys Val Leu Ile Tyr
            180                 185                 190 tgg gca tcc act agg gaa tct gga gtc cct gat cgc ttc aca ggc agt         624
Trp Ala Ser Thr Arg Glu Ser Gly Val Pro Asp Arg Phe Thr Gly Ser
        195                 200                 205 gga tct ggg aca gat ttc act ctc acc atc agc agt gtg cag gct gaa         672
Gly Ser Gly Thr Asp Phe Thr Leu Thr Ile Ser Ser Val Gln Ala Glu
    210                 215                 220 gac ctg gca gtt tat tac tgc aag caa tct tat aat cta ccg acg ttc         720
Asp Leu Ala Val Tyr Tyr Cys Lys Gln Ser Tyr Asn Leu Pro Thr Phe
225                 230                 235                 240 ggc ggg ggc acc aag ctg gaa atc aaa                                     747
Gly Gly Gly Thr Lys Leu Glu Ile Lys
                245
```

<210> SEQ ID NO 4
<211> LENGTH: 249
<212> TYPE: PRT
<213> ORGANISM: Mus musculus

<400> SEQUENCE: 4

```
Gln Val Lys Leu Gln Glu Ser Gly Ala Glu Leu Val Arg Ser Gly Ala
1               5                   10                  15

Ser Val Asn Leu Ser Cys Thr Ala Ser Gly Phe Asn Ile Lys Asp Tyr
            20                  25                  30

Tyr Met His Trp Val Lys Gln Arg Pro Glu Glu Gly Leu Glu Trp Ile
        35                  40                  45

Gly Tyr Ile Asp Pro Glu Ser Gly Glu Thr Glu Tyr Ala Pro Asn Phe
    50                  55                  60

Gln Gly Lys Ala Thr Val Thr Ala Asp Thr Ser Ser Asn Thr Ala Tyr
65                  70                  75                  80

Leu His Leu Ser Ser Leu Thr Ser Glu Asp Thr Thr Val Tyr Tyr Cys
                85                  90                  95

Asn Ala Val Ile Tyr Tyr Glu Tyr Asp Gly Tyr Ala Leu Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Ser Asp Ile Glu Leu Thr Gln Ser
    130                 135                 140

Pro Ser Ser Leu Ala Val Ser Ala Gly Glu Lys Val Ala Met Ser Cys
145                 150                 155                 160

Lys Ser Ser Gln Ser Leu Phe Asn Ser Arg Thr Arg Lys Asn Tyr Leu
                165                 170                 175

Ala Trp Tyr Gln Gln Lys Pro Gly Gln Ser Pro Lys Val Leu Ile Tyr
            180                 185                 190

Trp Ala Ser Thr Arg Glu Ser Gly Val Pro Asp Arg Phe Thr Gly Ser
        195                 200                 205

Gly Ser Gly Thr Asp Phe Thr Leu Thr Ile Ser Ser Val Gln Ala Glu
    210                 215                 220
```

```
Asp Leu Ala Val Tyr Tyr Cys Lys Gln Ser Tyr Asn Leu Pro Thr Phe
225                 230                 235                 240

Gly Gly Gly Thr Lys Leu Glu Ile Lys
                245
```

ANTI-P53 SINGLE-CHAIN ANTIBODY FRAGMENTS AND THEIR USES

The present invention relates to a process for restoring a p53-dependent transactivation activity in cells exhibiting a mutated p53 protein which is devoid of its transcriptional factor function or whose transcriptional factor function is diminished. More particularly, the process of the invention is based on using single-chain antibodies which are able to bind the mutated p53 protein specifically. It also relates to novel molecules which are able to bind p53 proteins specifically and efficiently and which additionally make it possible to restore a p53 activity in tumour cells, as well as to the nucleic acids encoding these molecules and to the vectors containing them. This process, and the molecules of the invention, can be used in vitro or ex vivo to study the mechanism of action of p53 and its mutated forms or to purify the p53 proteins. They also offer in-vivo uses, in particular in therapeutic approaches for restoring p53 activity in pathological contexts such as, in particular, cancers.

The wild-type p53 protein is involved in the regulation of the cell cycle and in the maintenance of the integrity of the genome of the cell. This protein, whose principal function is that of being an activator of the transcription of certain genes, is able, by means of a process which is still not well defined, to block the cell in the G1 phase of the cell cycle when mutations appear during replication of the genome and to set in motion a certain number of processes for repairing the DNA. Furthermore, if there is a fault in these repair processes or if mutational events appear which are too numerous to be corrected, this protein is able to induce the phenomenon, termed apoptosis, of programmed cell death. In this way, the p53 protein acts as a tumour suppressor by eliminating cells which have differentiated in an abnormal manner or whose genome has been damaged.

This main function of p53 depends on its transcription factor function, in other words on its double ability to recognize specific sequences in the genomic DNA and to recruit the general machinery of transcription.

The p53 protein comprises 393 amino acids which define 5 functional domains:

the transcription activator domain, which consists of amino acids 1 to 73 and which is able to bind certain factors of the general transcription machinery such as the protein TBP. This domain is also the site of a certain number of post-translational modifications. It is also the site for a large number of interactions between the p53 protein and a large number of other proteins, in particular the cell protein mdm2 or the Epstein-Barr virus (EBV) protein EBNA5, which proteins are able to block the function of the wild-type protein. Furthermore, this domain possesses amino acid sequences which are termed PEST and which are susceptible to proteolytic degradation.

the DNA-binding domain, which is located between amino acids 73 and 315. The conformation of this central domain of p53 regulates the recognition of DNA sequences which are specific for the p53 protein. This domain is the site of two types of alteration which affect the function of the wild-type protein:

(i) interaction with proteins, such as the "large T" antigen of the SV40 virus or the E6 viral proteins of the HPV16 and HPV18 viruses, which block the function of p53 and which are able to bring about its degradation by the ubiquitin system. This latter interaction can only be effected in the presence of the cell protein E6ap (enzyme E3 of the ubiquitinilation cascade).

(ii) point mutations which affect the function of p53 and almost all of which are located in this region.

the nuclear localization signal, which consists of amino acids 315 to 325 and which is essential for correctly directing the protein to the compartment where it will exert its main function.

the oligomerization domain, which consists of amino acids 325 to 355. This 325 to 355 region forms a structure of the type: $\beta$ pleated sheet (326-334)-bend (335-336)-$\alpha$-helix (337-355). The functional alterations which are located in this region are essentially due to interaction of the wild-type protein with the different mutant forms, which forms can produce variable effects on the function of the wild-type protein.

the regulatory domain, which consists of amino acids 365 to 393 and which is a site of various post-translational modifications (glycosylations, phosphorylations, RNA binding, etc.) which modulate the function of the p53 protein in a positive or negative manner. This domain plays an extremely important role in modulating the activity of the wild-type protein.

Operation of the p53 protein can be disrupted in a variety of ways.

its function can be blocked by various factors such as, for example, the SV40 virus "large T" antigen, the Epstein-Barr virus EBNA5 protein or the mdm2 cell protein.

the protein can be destabilized by increasing its susceptibility to proteolysis, in particular by means of interaction with the E6 protein of the human papilloma viruses HPV16 and HPV18, which protein promotes entry of p53 into the ubiquitinilation cycle. In this case, interaction between these two proteins can only be effected by means of the prior binding of a cell protein, the E6ap protein, about whose binding site little is known.

point mutations can arise within the p53 gene.

one or both of the p53 alleles can be deleted.

The last two types of modification are found in about 50% of the different types of cancer. In this regard, the mutations of the gene for p53 which have been listed in cancerous cells affect a very large part of the gene encoding this protein and result in a variety of changes to the operation of this protein. However, it can be noted that the great majority of these mutations are located in the central part of the p53 protein, which part is known to be the region of contact with the genomic sequences which are specific for the p53 protein. This explains why the principal characteristic of most of the mutants of the p53 protein is that of no longer being able to bind to the DNA sequences which are recognized by the wild-type protein and consequently no longer being able to carry out their role of transcription factor. In other respects, some mutants appear to have acquired novel functions such as the activation of certain genes at the transcriptional level.

At present, all these various modifications are grouped into three categories:

so-called weak mutants, the product of which is a non-functional protein which, when only one of the two alleles is mutated, has no effect on the operation of the wild-type protein which is encoded by the other allele. The main representatives of this category are the mutants H273 and W248, with the latter being specific for the Li-Fraumeni familial syndrome of hypersusceptibility to cancerous ailments.

the dominant-negative mutants, the product of which is a nonfunctional protein which, when only one of the two alleles is mutated, and by means of interaction with the wild-type protein, is able to block operation of the latter protein by means of forming inactive mixed oligomers which are no longer able to bind to the DNA sequences which are specific for the wild-type protein. The principal representative of this category is the mutant G281.

the dominant-oncogenic mutants, the product of which is a protein which is able, on the one hand, to block the function of the wild-type protein, like the mutants of the previous category, and, on the other hand, to promote, by means of mechanisms which are not well understood, tumour development, thereby exhibiting a gain in function. The main representative of this category is the mutant H175.

In view of its anti-tumour and apoptotic properties, and its involvement in a large number of pathologies of the hyperproliferative type, the wild-type p53 gene has been used in gene therapy and cell therapy approaches. It has, in particular, been proposed that certain hyperproliferative pathologies, in particular cancers, be treated by administering the wild-type p53 gene in vivo, thereby restoring p53 functions. Administration may preferentially be effected by means of viral vectors, in particular adenoviral (WO94/24297) or retroviral (WO94/06910) vectors. Thus, it was demonstrated that introduction of a nucleic acid encoding the wild-type p53 protein enabled normal regulation of cell growth to be partially restored (Roth et al., Nature Medicine 2 (1996) 985). Alternative strategies, which are based on using chimeric molecules which possess properties of the p53 type, have also been developed (PCT/FR96/01111).

Another approach aimed at restoring the functions of the wild-type p53 protein is based on reversion of the endogenous mutated proteins towards a wild-type phenotype, that is to say exhibiting the tumour-suppressing and apoptotic properties of the wild-type p53. This approach ensues from the demonstration that the losses in function of the p53 mutants are due to a conformational change of the protein, which change is induced by the mutation(s). In this regard, application WO94/12202 demonstrates that a specific monoclonal antibody, which is designated pAb421 and which is directed against the p53 protein, is able to restore the function of binding to DNA in vitro to a certain class of mutants which are frequently represented in human cancers. However, the use of this type of compound presents significant drawbacks which are linked, in particular, to the large quantity of antibody required (and therefore to the associated problems of production/purification) and to their poor intracellular penetration.

The present application describes a more effective approach for restoring the wild-type properties of a mutant of the p53 protein. The present application describes, in particular, the construction of ligands which are especially specific for the p53 protein and which have properties which are advantageous for restoring the wild-type p53 functions. More particularly, the present application describes the construction of single-chain antibodies (ScFvs), in particular the molecule 11D3, which are specific for the p53 protein. The present application furthermore demonstrates that the ScFvs are able to recognize p53, are able to be expressed efficiently within a tumour cell and are able to reactivate a part of the transactivating function of a certain class of p53 mutants.

As compared with the methods of the prior art, this molecule exhibits significant advantages, in particular the possibility of being expressed in situ, in substantial quantities, in a tumour cell. The results which are presented below are all the more unexpected because loses of affinity had often been observed when passing from a conventional antibody to an ScFv. Furthermore, the applicant has demonstrated that it in possible to express the ScFvs in the appropriate intracellular compartments, thereby enabling optimum biological activity to be obtained.

The invention initially relates, therefore, to a process for restoring a p53-dependent transactivation activity in cells possessing a mutated p53 protein, which process comprises introducing, into the said cell, a single-chain antibody which is able to bind the mutated p53 protein specifically. Advantageously, the process of the invention comprises introducing, into the cell, a nucleic acid which comprises a sequence encoding the said single-chain antibody under the control of a promoter which is able to function in the cell. Another aspect of the invention relates to the use of a single-chain antibody which is able to bind a mutated p53 protein specifically for modifying the conformation of the said protein. The invention also relates to the use of a single-chain antibody which is able to bind a mutated p53 protein specifically for preparing a pharmaceutical composition which is intended for treating hyperproliferative disorders in which a mutated p53 protein is involved, as well as to the use of a nucleic acid encoding a single-chain antibody which is able to bind a mutated p53 protein specifically for preparing a pharmaceutical composition which is intended for treating the hyperproliferative disorders in which a mutated p53 protein is involved.

The process of the invention is therefore based in part on constructing and vectorizing single-chain antibodies which are able to bind a mutated p53 protein specifically and introducing these antibodies into cells. The single-chain antibodies (ScFvs) essentially consist of a VH region which is linked to a region by an arm. The construction of ScFvs and of nucleic acid sequences which encode such modified antibodies has been described, for example, in patent U.S. Pat. No. 4,946,778 or in applications WO 94/02610 and WO 94/29446, which are hereby incorporated into the present application by reference.

The present application more specifically describes the creation of a hybridoma library which produces antibodies directed against p53 and the construction, from this library, of corresponding ScFvs. It also describes the cloning of the corresponding nucleic acids into expression vectors and their transfer into cells. It also demonstrates that this transfer enables the DNA-binding activity of p53 mutants, and their transactivating activity, to be efficiently restored in vivo.

More particularly, the process of the invention employs ScFvs which are able specifically to bind an epitope which is present in the C-terminal region of p53 and which carries the oligomerization domain and the regulatory domain. In this regard, the present application also describes a test which enables the ScFvs possessing this property to be selected by means of the ELISA technique.

Even more preferably, the ScFvs employed in the process of the invention are able specifically to bind an epitope which is present in the C-terminal region of p53 between residues 320–393. In this regard, the application describes, as a specific example, the construction and expression of the ScFv ScFv 421, having the sequence SEQ ID No. 1, and of 11D3, having the sequence SEQ ID No. 2.

The process of the invention can be applied generally to mutated p53 proteins which have lost, totally or partially, the ability to bind DNA, and the process of the invention enables this ability to be restored. More particularly, the process of the invention can be applied to mutated p53 proteins which have lost, totally or partially, the transcriptional factor function of p53, and it enables this function to be restored. The degree of restoration may be total or partial. Advantageously, it is sufficient to enable the mutant to exert a tumour-suppressing function by means of blocking the cell cycle and/or by means of inducing apoptosis. The process of the invention therefore makes it possible to restore, at least partially, a tumour-suppressing activity in cells which possess endogenous mutated p53 proteins which are devoid of this activity. Advantageously, these latter proteins are mutated proteins which are present in tumour cells. As indicated above, different mutated forms of the p53 protein have been demonstrated in tumour cells. The proteins p53H273, p53W248 and p53G281 may be mentioned by way of example. The examples which are presented below demonstrate, in particular, that the process of the invention makes it possible to modify the conformation, and the biological properties, of these mutants both in vitro and in vivo. In particular, these examples demonstrate that the ScFvs 421 and 11D3 are able to restore the ability of mutants 273 and 248 to bind DNA specifically and to induce p53-dependent transactivation.

The process of the invention can be implemented in vitro, ex vivo or in vivo. In vitro or ex vivo, the process and the molecules of the invention can make it possible, for example, to study the mechanism of action of p53 and its mutated forms. Furthermore, the molecules of the invention can be used to detect or purify p53 proteins, for example by coupling the molecules to a support, and bringing them into contact with a solution containing p53 proteins, with this then being followed, if necessary, by visualization of the complexes which have been formed or by an elution. In vivo, in particular in humans, they can make it possible, in pathological contexts such as hyperproliferative disorders in which a deficiency in p53 activity is observed, for this function to be restored. In this regard, the process can be employed in association with other above-mentioned approaches (introduction of a wild-type p53 gene) or else in association with chemotherapy (WO96/22101). Still in vivo, the process and the molecules of the invention can be used in animals, for example in order to determine the levels at which the ScFvs are expressed and to evaluate the possibility of a therapeutic approach for use in humans.

Advantageously, the cell which possesses a mutated p53 protein is a mammalian tumour cell. In this regard, those cells which may more particularly be mentioned are the cells of lung (in particular not small-cell), colon, liver, brain, head and neck cancers and, more generally, any cancer in which a mutated form of the p53 protein is observed. Advantageously, the cell is a human tumour cell in which a p53H273, p53W248 and/or p53G281 mutant is observed (lung, colon, brain, head and neck, liver). The applicability of the process of the invention to a particular cell can easily be determined using the following methodology: the cell is first of all examined for the presence of a mutated p53 protein. This protein is then examined in order to determine the nature of the mutation. If this mutation is a known mutation, in particular a mutation listed above, the cell can be regarded as being susceptible to treatment by the process of the invention. If the mutation is an unlisted mutation, various approaches are possible. The mutated protein can first of all be isolated (or synthesized artificially) and tested, as described in the examples, for its behaviour in vitro and in vivo in the presence of ScFv. This enables the ScFv to be identified which is appropriate for restoring the deficient functions of this protein. Another approach consists in directly testing the ScFvs on a culture of cells in order to determine the biological efficacy of the ScFvs.

In order to implement the process of the invention, the ScFv is advantageously introduced into the cell, in vitro, ex vivo or in vivo, in the form of a vector carrying a nucleic acid which encodes the said ScFv under the control of a promoter which is able to function in the said cell.

The promoter is advantageously chosen from among the promoters which are able to function in mammlian cells, preferably human cells. More preferably, the promoter is a promoter which enables a nucleic acid to be expressed in a hyperproliferative (cancerous, restenosis, etc.) cell. Various promoters may be employed in this regard. The promoter can, for example, be the native promoter of the p53 gene. The promoters can also be regions of different origin (which are responsible for expressing other proteins or even synthetic proteins). The promoter can thus be any promoter or derived sequence which stimulates or represses the transcription of a gene specifically or non-specifically, inducibly or non-inducibly and strongly or weakly. Particular mention may be made of the promoter sequences of eukaryotic or viral genes. For example, the promoter sequences can be promoter sequences which are derived from the genome of the target cell. Eukaryotic promoters which may in particular be used are ubiquitous promoters (promoter of the HPRT, PGK, α-actin, tubulin, etc. genes), promoters of the intermediate filaments (promoter of the GFAP, desmin, vimentin, neurofilament, keratin, etc. genes), promoters of therapeutic genes (for example the promoter of the MDR, CFTR, factor VIII, ApoAI, etc. genes), tissue-specific promoters (promoter of the pyruvate kinase, villin, intestinal fatty acid-binding protein, smooth muscle α-actin, etc. gene) or else promoters which respond to a stimulus (steroid hormone receptor, retinoic acid receptor, etc.). Similarly, the promoter sequences can be promoter sequences which are derived from the genome of a virus, such as, for example, the promoters of the adenovirus E1A and MLP genes, the CMV early promoter, or else the RSV LTR promoter, etc. Furthermore, these promoter regions can be modified by the addition of activating sequences, regulatory sequences or sequences which permit an expression which is tissue-specific or mainly tissue-specific.

As indicated above, the present application also describes novel molecules which have particularly advantageous properties of binding and reverting mutated p52 proteins. More precisely, the invention describes the construction, the vectorization and the transfer into cells of specific ScFvs (11D3 and 421). The nucleic acid sequence and peptide sequence of the 421 ScFv are given in SEQ ID No. 1 and SEQ ID No. 2. The nucleic acid sequence and peptide sequence of the 11D3 ScFv are given in SEQ ID NO: 3 and SEQ ID NO: 4. The examples which follow demonstrate the particularly advantageous ability of these molecules (i) specifically to bind mutated p53 proteins in the C-terminal region, (ii) to restore the ability of these mutated proteins to bind DNA, and (iii) to restore the ability of these proteins to activate transcription. The examples furthermore demonstrate that these molecules are correctly expressed in tumour cells, thereby enabling the molecules to be advantageously used in the context of hyperproliferative disorders. Moreover, the properties of the ScFvs of the invention can also be improved. In particular, it is known that the affinity of the ScFvs is influenced by the CDR regions (underlined in the sequence) and can be improved by means of routine mutagenesis/selection experiments. Thus, mutagenesis carried out on antibodies has been described, for example, by Marks et al. (Bio/Technology, 10, 779–783, 1992) and by Winter G. and Milstein C. (Nature, 349, 293–299, 1991). The techniques described in these references can be applied to preparing variants of the ScFvs which have an affinity which is modified in accordance with the invention. Selection can then be effected under the conditions described in the examples.

The invention therefore also relates to the 11D3 molecule, whose peptide sequence is depicted in SEQ ID No. 4, and to any variant which exhibits a modification in the CDR regions which retains the ability to bind p53 proteins. The modification can consist of a deletion, a substitution or an insertion of one or more residues in the CDR regions. Advantageously, the modification affects less than 10 residues.

The present invention also relates to any nucleic acid which encodes ScFv 11D3 or any variant as defined above.

The nucleic acid according to the invention can be a ribonucleic acid (RNA) or a deoxyribonucleic acid (DNA). Advantageously, it is a complementary DNA (cDNA). It can be of human, animal, viral, synthetic or semi-synthetic origin. It can be obtained in different ways, in particular by means of chemical synthesis using the sequences presented in the application and, for example, a nucleic acid synthesizer. It can also be obtained by screening libraries with specific probes, in particular those described in the application. It can even be obtained by means of mixed techniques including chemical modification (elongation, deletion, substitution, etc.) of sequences which have been obtained by screening libraries. In a general manner, the nucleic acids of the invention can be prepared by any technique known to the skilled person (see, in particular, the techniques described in patents U.S. Pat. No. 4,946,778 and WO94/02610, which patents are incorporated into the present application by reference). A standard strategy for constructing nucleic acids encoding an ScFv is the following: the cDNA molecules encoding the VH and VL regions are obtained from the hybridoma which is producing the chosen anti-p53 antibody. For this, the total RNA of the hybridoma is extracted and subjected to a reverse transcription reaction using random hexamers as primers. The use of this type of primer makes it possible to avoid using primers which are specific for immunoglobulins. The resulting cDNA clones are of a length which is sufficient for cloning the V regions. When they represent a fraction of the total cDNA present which is too low, a preliminary amplification reaction can be carried out in order to produce sufficient DNA for the cloning. For this, the cDNA molecules encoding the VH and VL regions are amplified separately. The primers employed are oligonucleotides which hybridize to the opposite ends of the variable regions of each chain (H and L). The amplification product obtained using the primers which are specific for the heavy chains and the amplification product obtained using the primers which are specific for the light chains are then purified. After purification, the cDNA molecules encoding the VH and VL regions of the antibody are joined together into a single chain using nucleotide arm (L). The nucleotide arm was constructed such that one of the ends binds to the 3' end of the cDNA encoding the VH region and the other binds to the 5' end of the cDNA encoding the VL region. The sequence of the arm encodes the peptide (G4S)3. The assembled sequence, of approximately 700 bp, contains the VH-L-VL assembly, whose sequences are depicted in SEQ. ID No. 1 and SEQ ID No. 3, for example, in the form of an NcoI/NotI fragment.

Preferably, the nucleic acid according to the invention is a cDNA or an RNA.

The nucleic acid according to the invention is advantageously chosen from:
(a) all or part of the sequence SEQ ID No. 2 or of its complementary strand,
(b) any sequence which hybridizes with the (a) sequences and which encodes an ScFv which is able specifically to bind the p53 protein, preferably within the C-terminal region,
(c) the variants of (a) and (b) which result from the degeneracy of the genetic code.

The present invention also relates to any expression cassette which comprises a nucleic acid as defined above, a promoter which enables it to be expressed and a transcription termination signal.

In the process of the invention, the acid is advantageously introduced into the cells by means of an administration vector which makes it possible to improve (i) the efficiency of cell penetration, (ii) targeting and/or (iii) extracellular and intracellular stability.

In one particularly preferred embodiment of the present invention, the nucleic acid is incorporated into a vector which can be of chemical (liposome, nanoparticle, peptide complex, cationic lipid or polymer, etc.), viral (retrovirus, adenovirus, herpes-virus, AAV, vaccinia virus, etc.) or plasmid origin.

The use of viral vectors is based on the natural transfection properties of viruses. Thus, it is possible to use, for example, adenoviruses, herpes-viruses, retroviruses and adenoassociated viruses. These vectors are found to be particularly efficient with regard to transfection. In particular, the ability of adenoviruses and retroviruses to infect tumour cells make these viruses the vectors of choice in the context of the invention. In this regard, in a preferred embodiment of the invention, the nucleic acid is introduced in the form of a retroviral vector, that is to say in the form of a defective recombinant retrovirus whose genome comprises a nucleic acid encoding an ScFv as defined above. In another preferred embodiment of the invention, the nucleic acid is introduced in the form of an adenoviral vector, that is to say in the form of a defective recombinant adenovirus whose genome comprises a nucleic acid encoding an ScFv as defined above.

The vector according to the invention can also be a non-viral agent which is able to promote the transfer and expression of nucleic acids in eukaryotic cells. Synthetic or natural chemical or biochemical vectors represent an attractive alternative to natural viruses, in particular for reasons of convenience, of safety and also because of the absence of any theoretical limit with regard to the size of the DNA to be transfected. These synthetic vectors have two main functions, i.e. to compact the nucleic acid to be transfected and to promote its binding to the cell and its passage through the plasma membrane and, if the need arises, the two nuclear membranes. In order to compensate for the polyanionic nature of the nucleic acids, the non-viral vectors all possess polycationic charges. In a particular process according to the invention, the vector is a chemical or biochemical vector.

The invention also relates to any composition which comprises at least one nucleic acid as defined above.

It also relates to any composition which comprises at least one vector as defined above.

It also relates to any composition which comprises at least one ScFv as defined above.

It also relates to compositions which comprise a nucleic acid or a vector as defined above and a nucleic acid or a vector encoding wild-type p53, for simultaneous combined use or for combined use which is spaced out in time.

On account of their antiproliferative properties, the pharmaceutical compositions according to the invention are very particularly suitable for treating hyperproliferative disorders such as, in particular, cancers and restenosis. The present invention consequently supplies a particularly efficient method for destroying cells, in particular hyperproliferative cells.

The invention can be employed in vitro or ex vivo. In this case, it essentially consists in incubating the cells in the presence of one or more nucleic acids (or of a vector or cassette or directly of the ScFv). Doses of from 0.01 to 1000 μg of vector per $10^6$ cells, or an MOI of from 0.1 to 1000 for a viral vector can be employed.

In vivo, it consists in administering, to the organism, an active quantity of a vector (or of a cassette) according to the invention, preferably directly at the site to be treated (in particular tumour). In this regard, the invention also relates to a method for destroying hyperproliferative cells, which method comprises bringing the said cells, or some of these cells, into contact with a nucleic acid as defined above. For an in-vivo use, the nucleic acid or the vector which is employed in the present invention can be formulated with a view to being administered by the topical, oral, parenteral, intranasal, intravenous, intramuscular, subcutaneous, intraocular, transdermal, etc. route. Preferably, the nucleic acid or the vector is employed in an injectable form. It can therefore be mixed with any excipient which is pharmaceutically acceptable for an injectable formulation, in particular for an injection directly into the site to be treated. The compositions can, in particular, be sterile, isotonic solutions, or dry, in particular lyophilized, compositions which, by means of the addition of sterilized water or physiological saline, as the case may be, enable injectable solutions to be constituted. A direct injection of the nucleic acid into the tumour of the patient is advantageous since this makes it possible to concentrate the therapeutic effect at the level of the affected tissues. The doses of nucleic acid employed can be adjusted in accordance with various parameters, particularly in accordance with the gene, the vector, the mode of administration employed, the pathology concerned or else the sought-after duration of the treatment. Advantageously, the doses which are administered in vivo are between $10^6$ and $10^{10}$ pfu for a viral vector such as an adenovirus. Furthermore, repeated administrations can also be envisaged.

Still in vivo, the process and the molecules of the invention can be used to study the mechanisms of action of p53 and to determine the potential of the ScFvs on animal models.

The present invention is advantageously employed in vivo for destroying hyperproliferated cells (i.e. abnormally proliferating cells). It can thus be applied to the destruction of tumour cells or of smooth muscle cells of the vascular wall (restenosis). It is very particularly appropriate for treating cancers in which a mutant of p53 is observed. By way of example, mention may be made of adenocarcinomas of the colon, cancers of the thyroid, carcinomas of the lung, myeloid leukaemias, colorectal cancers, cancers of the breast, cancers of the lung, gastric cancers, cancers of the oesophagus, B lymphomas, ovarian cancers, cancers of the bladder, glioblastomas, hepatocarcinomas, cancers of the bones, of the skin or of the pancreas, or else cancers of the kidney and of the prostate, cancers of the oesophagus, cancers of the larynx, head and neck cancers, HPV-positive anogenital cancers, EBV-positive cancers of the nasopharynx, cancers in which the cell protein mdm2 is overexpressed, etc.

The present invention is described in more detail in the examples which follow and which should be regarded as being illustrative and not limiting.

FIGURE LEGENDS

FIG. 1: Strategy for screening the antibodies.

FIG. 2: Demonstration of the ability of the antibodies to retard the migration of p53 on a gel.

Figure 3:
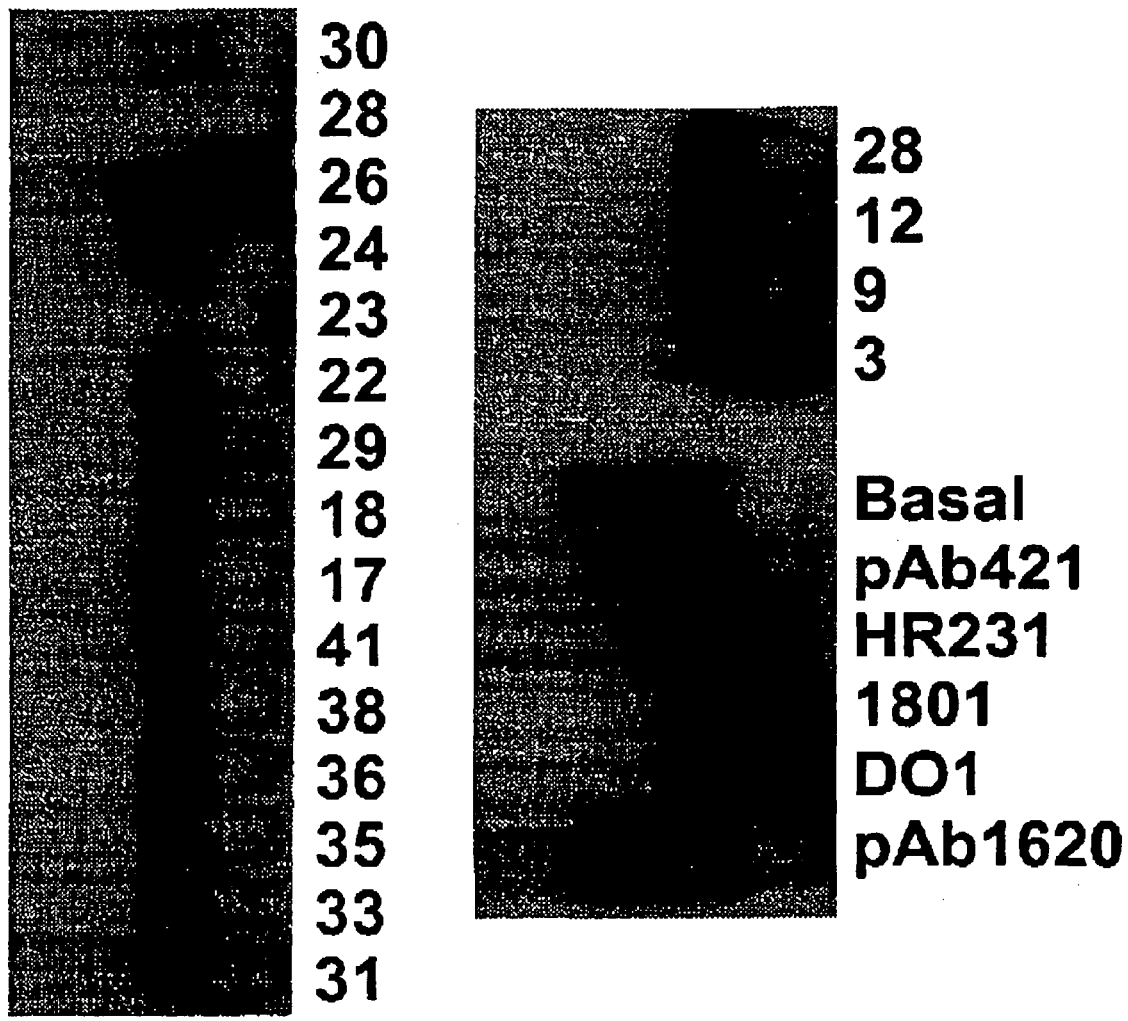

FIG. 3: Demonstration of the ability of the antibodies to retard the migration of p53H273 on a gel.

Figure 4:
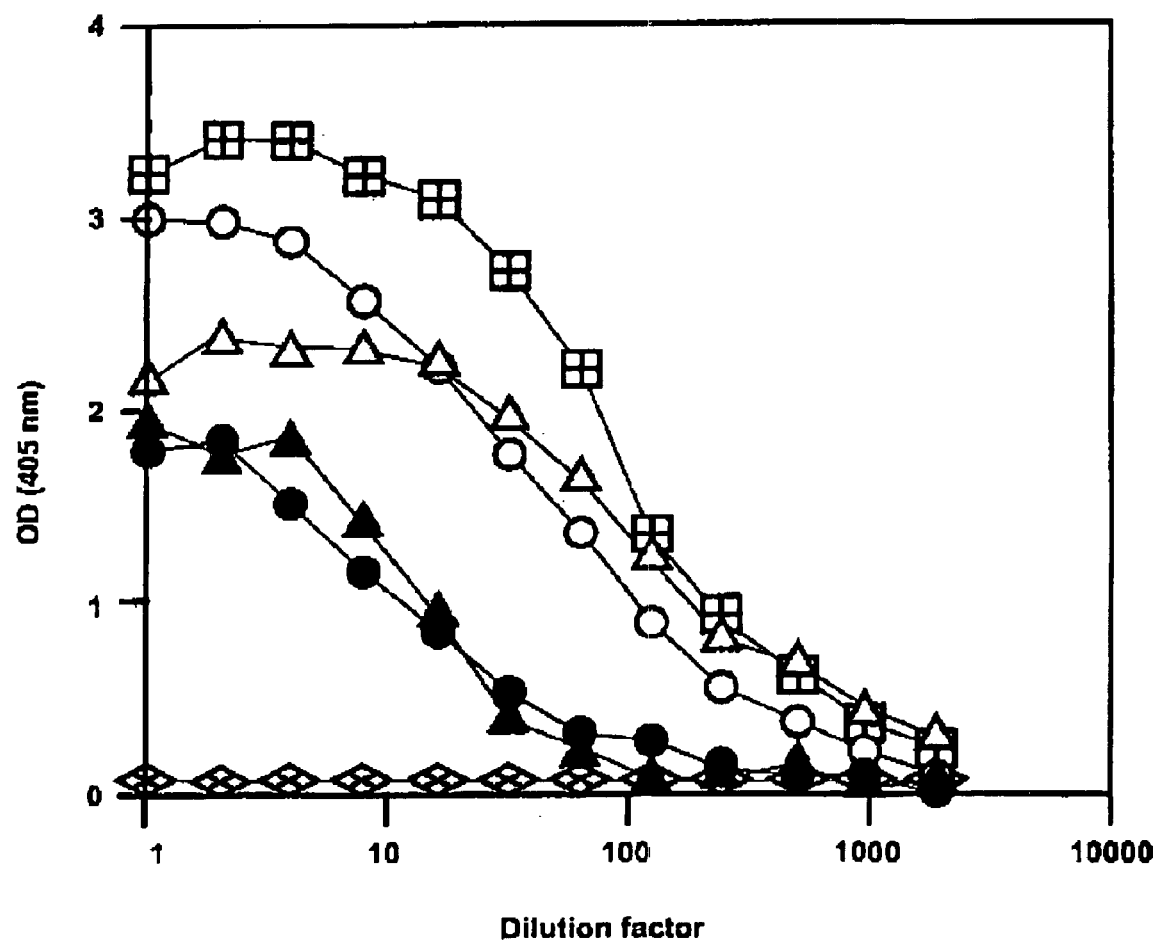

FIG. 4: Use of ELISA to demonstrate the association of the ScFvs with wild-type p53. Filled circles: IgG 11D3 (1 μg/ml initially); open circles: IgG 421 (1 μg/ml initially); squares: biotinylated polyclonal serum (1 μg/ml initially); filled triangles: ScFv 11D3-myc (diluted ½ initially); empty triangles: ScFv 421-myc (diluted ½ initially); diamonds: irrelevant ScFv (anti-CD3, diluted ½ initially).

Figure 5:
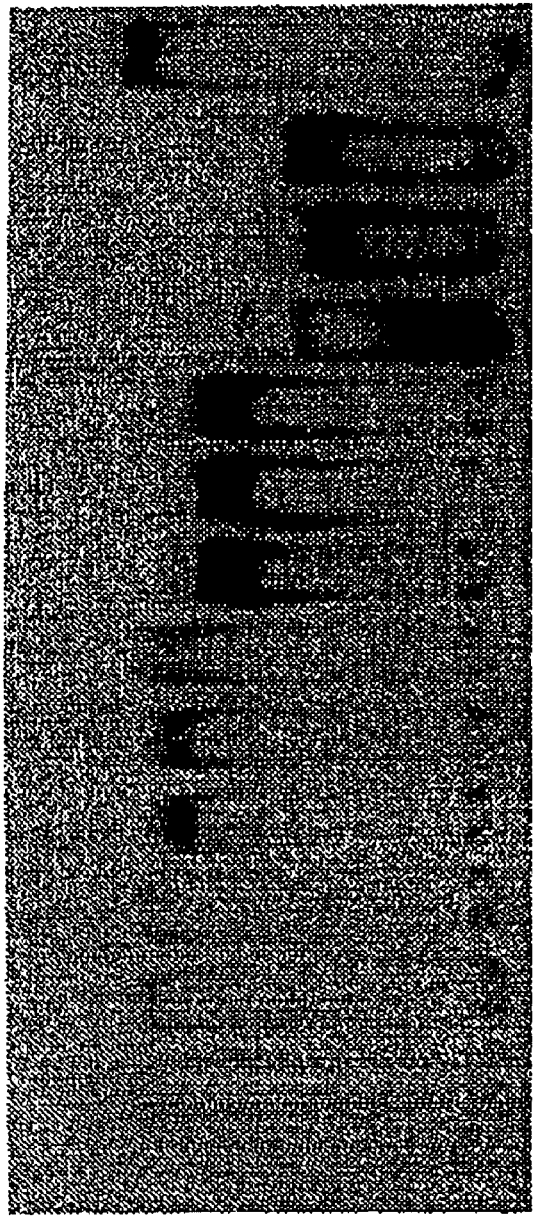

FIG. 5: Demonstration of gel retardations induced by the ScFvs.

Figure 6:
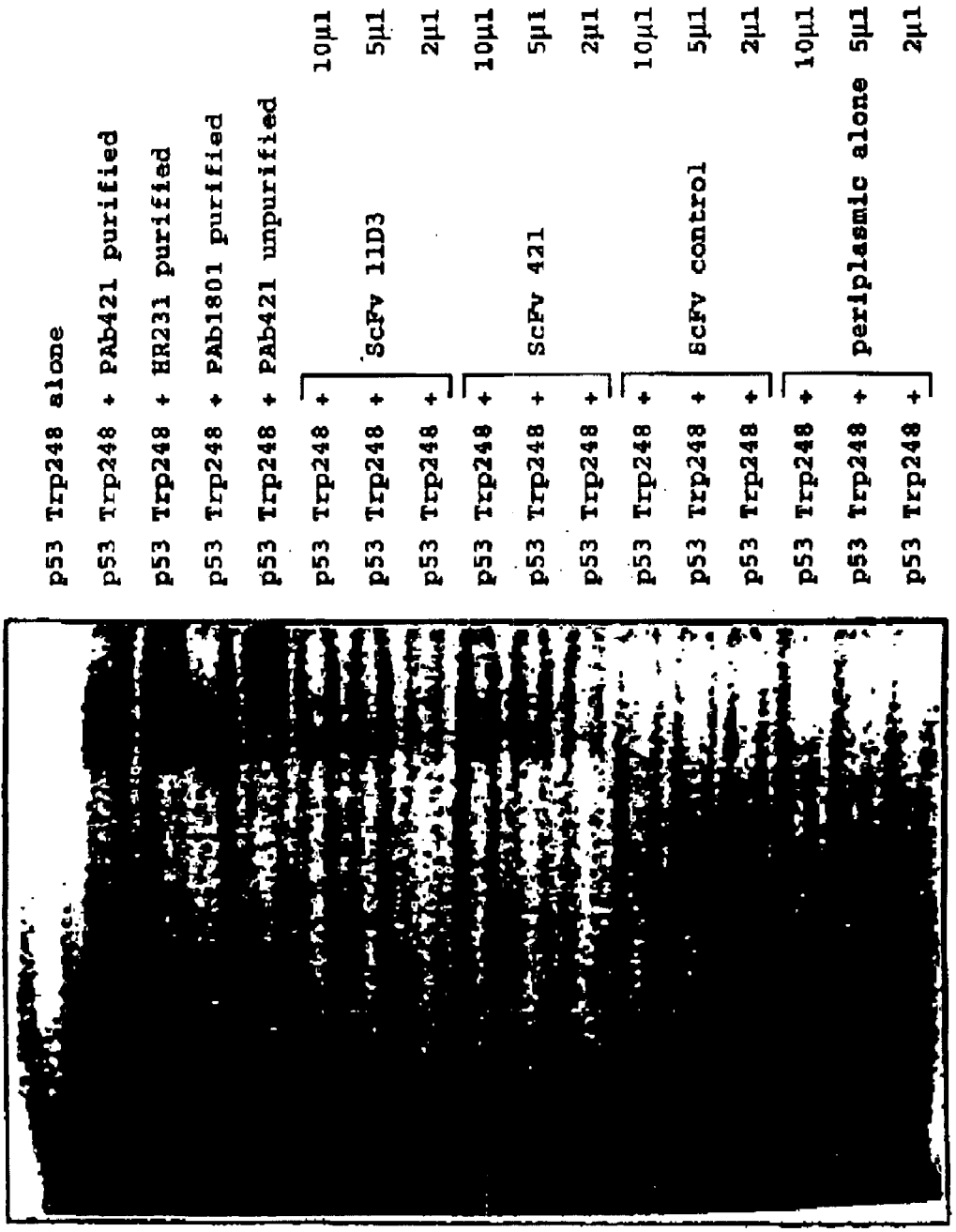

FIG. 6: Restoration of DNA-binding activity to mutants of p53.

Figure 7:
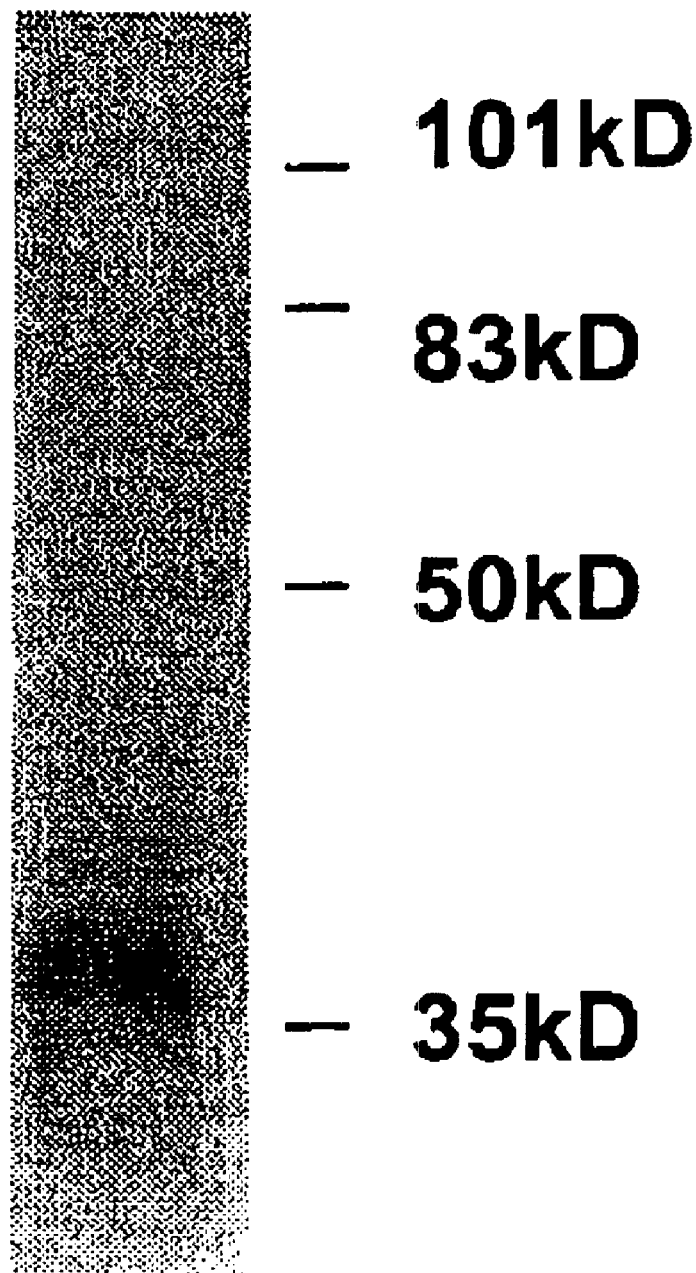

FIG. 7: Expression of ScFv421 in H1299 cells.

Figure 8:
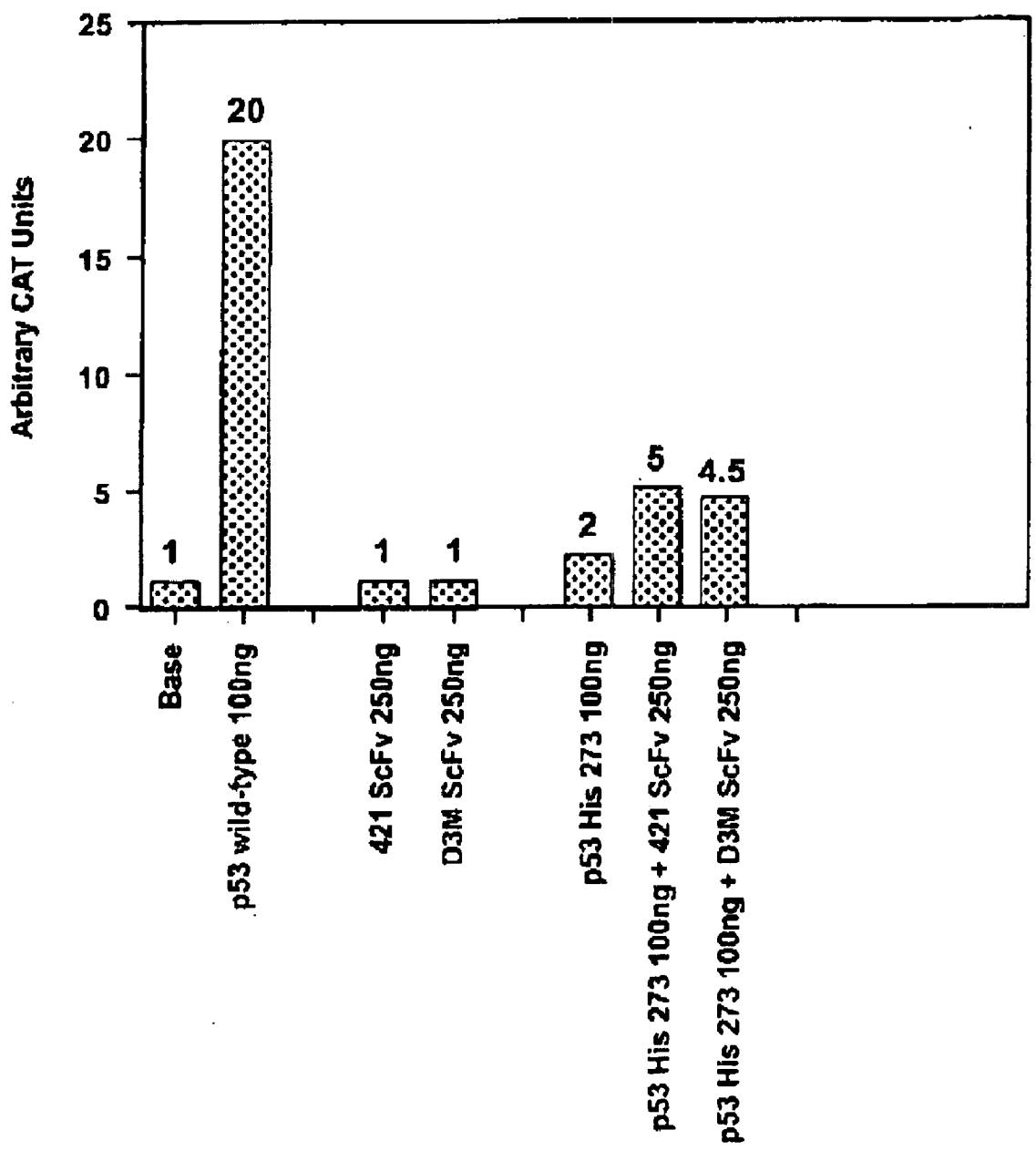

FIG. 8: Restoration of the transcriptional activity of mutant H273 in cell line H358.

Figure 9:
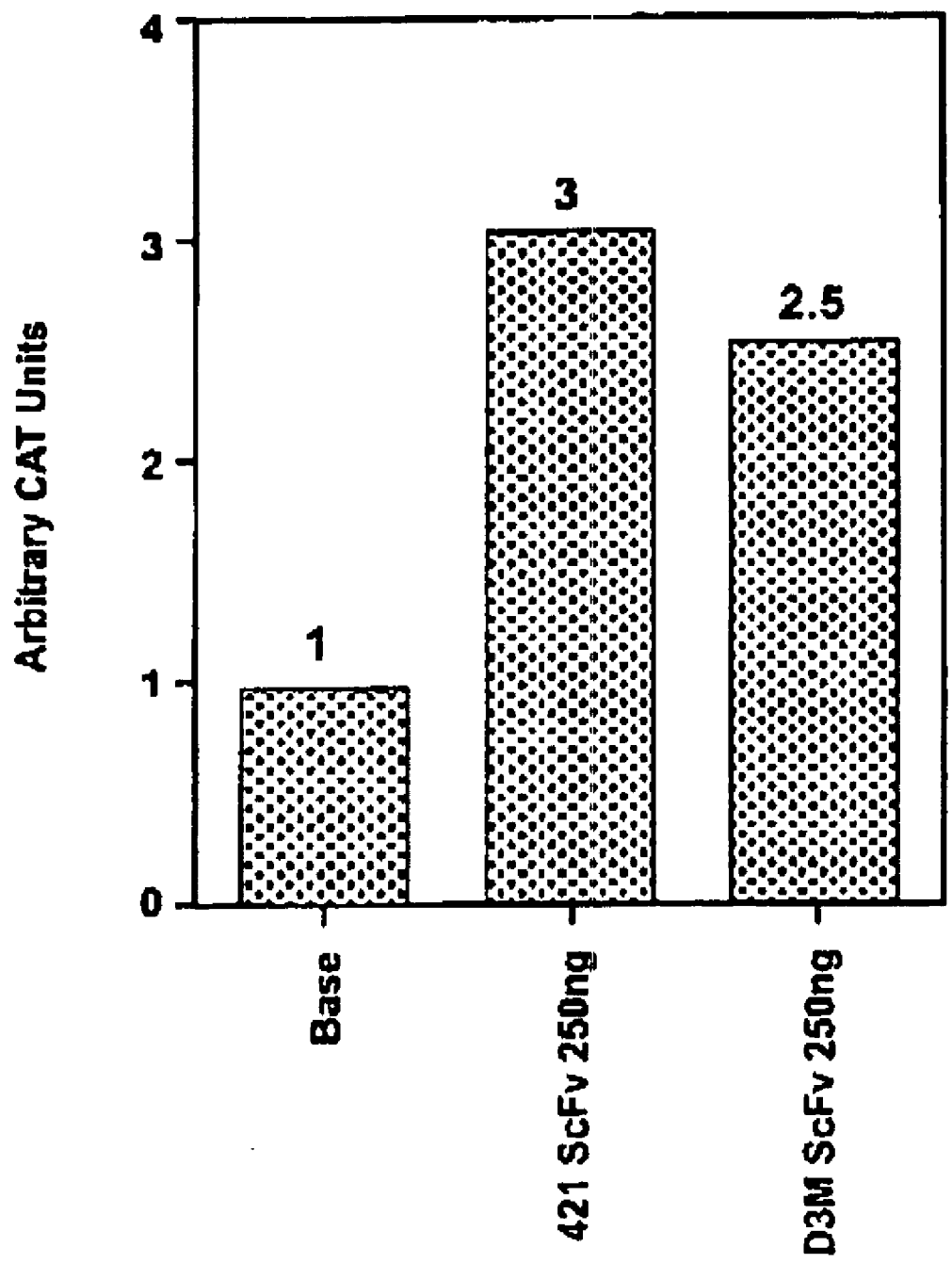

FIG. 9: Restoration of the transcriptional activity of mutant H273, which is endogenous in cell line HT29.

EXAMPLES

Example 1

Isolation and Screening of the Antibody 11D3

This example describes the preparation, isolation and selection of monoclonal antibodies which are directed specifically against the p53 protein, and which are able to activate the DNA-binding function of the mutated forms of p53.

1.1. Isolation of the Proteins Used for Immunizing the Mice and Screening of the Hybridomas The wild-type p53 protein, and various proteins, i.e. p53 H273, p53 W248 and p53 G281, corresponding to mutations of the wild-type p53 which are frequently found in tumour cells, were produced in *Spodoptera frugiperda* Sf9 insect cells which were infected with a recombinant baculovirus, and were purified by affinity chromatography on an agarose gel to which the polyclonal antibody PAb421 (Leveillard et al., EMBO J. 15, 1615–1623 (1996)) was coupled. The proteins corresponding to fragments 1–320 and 73–320 of the wild-type p53 protein were also produced in *Spodoptera frugiperda* Sf9 insect cells which were infected with a recombinant baculovirus following the instructions provided by the company Invitrogen. The complementary DNAs which were inserted into the pBlueBacIII transfer plasmid were generated using standard recombinant DNA techniques as described, for example, by Sambrook et al. (Sambrook, Fritsch & Maniatis: Molecular cloning, a laboratory manual, 2nd edition, 1989, Ed. Cold Spring Harbor Laboratory).

1.2. Isolation and Screening of the Hybridomas

The mice were immunized with an equimolar mixture of the three mutant p53 proteins described above and the hybridomas were isolated by following the procedural protocols described by Harlow and Lane (Harlow & Lane: Antibodies, a laboratory manual, 1988, Ed. Cold Spring Harbor Laboratory). Hybridomas producing monoclonal antibodies directed against the above-described mutant p53 proteins were selected by the method of capturing the antibody produced in the hybridoma culture medium in wells of 96-well PVC plates in which a quantity of 1 microgram of the equimolar mixture of the above-described three mutant p53 proteins had previously been immobilized, following the procedural protocols described by Harlow and Lane (Harlow & Lane: Antibodies, a laboratory manual, 1988, Ed. Cold Spring Harbor Laboratory). This first screening resulted in 317 positive hybridomas being selected. After two weeks of amplifying the hybridomas, the supernatants of the amplified hybridomas were firstly reevaluated using the above-mentioned antibody capture method (method 1) and were then classed using three screening methods which were in principle identical to that mentioned above apart from the fact that the nature of the immobilized proteins was different: either the purified wild-type p53 protein (method 2), or a protein extract derived from Sf9 cells which were producing the 1-320 fragment of the wild-type p53 (method 3), or a protein extract derived from Sf9 cells which were producing the 73-393 fragment of the wild-type p53 (method 4) were immobilized in the wells. The protein extracts were obtained by lysing the Sf9 cells, by means of repeated freezing/thawing in a phosphate buffer, and then ultracentrifuging the cell debris. Of the 317 amplified hybridoma supernatants, 162 no longer responded in method 1. The remaining 155 were all positive in method 2, including 33 (group A) which were negative in methods 3 and 4, 115 (group B) which were positive in method 3 and negative in method 4, and, finally, 7 (group C) which were positive in both these latter methods. The group B supernatants correspond to supernatants which contain an antibody whose epitope is located in the first 73 amino acids of p53. 77 supernatants of this group were found to be negative in method 2 when they were preincubated with the peptide (1 mg/ml) which corresponded to the sequence of the first 40 amino acids of p53. Isotyping the group A antibodies, the 38 group B antibodies which remain after eliminating the 77 antibodies mentioned above, and the group C antibodies enabled us to eliminate the IgM antibodies. These results are summarized in FIG. 1.

42 antibodies were then tested for their ability to induce a supershift in a p53/DNA complex. After having been purified on protein A/Sepharose, the antibodies were quantified. Gel retardation experiments were carried out by incubating 30 ng of purified wild-type p53 protein with a $^{32}$P-labelled DNA probe which represented a specific binding sequence for p53. 300 ng of the various antibodies were then added. The complexes were resolved on an acrylamide gel.

The results in FIG. 2 demonstrate that 27 of these antibodies were able to induce a supershift. 19 of these 27 were tested by substituting the His273 mutant for the wild-type p53 protein in the same gel retardation experiment (FIG. 3). These 19 antibodies all gave positive results. Antibody No. 26 gave a more pronounced retardation than did the others. This antibody was designated 11D3 and used in the subsequent experiments.

Example 2

Isolation of the ScFvs 421 and D3M

The ScFvs were isolated from hybridomas using standard molecular biological techniques which were based on PCR experiments carried out using degenerate primers which were specific for the VH and VL regions. The ScFv which was derived from the antibody 11D3 was designated D3M. Its sequence is depicted in SEQ ID No. 3. The sequence of ScFv421 is depicted in SEQ ID No. 1.

Example 3

Construction of Vectors for Expressing the ScFvs

This example describes the construction of vectors which can be used for transferring the nucleic acids of the invention in vitro or in vivo.

3.1. Construction of Plasmid Vectors 2 types of vector were used for constructing plasmid vectors.

The vector pSV2, which is described in DNA Cloning, A practical approach Vol. 2, D. M. Glover (Ed) IRL Press, Oxford, Washington DN, 1985. This vector is a eukaryotic expression vector. The nucleic acids encoding the ScFvs were inserted into this vector in the form of HpaI/EcoRV fragments. This placed them under the control of the promoter of the SV40 virus enhancer. All the constructs described in Example 2 were introduced into this vector in order to be tested in the different in vitro and in vivo evaluation systems.

The vector pCDNA3 (Invitrogen). This is also a eukaryotic expression vector. In this vector, the nucleic acids encoding the ScFvs of the invention are thus placed under the control of the CMV early promoter. All the constructs described in Example 2 were introduced into this vector in the form of a HindIII/NotI fragment.

3.2. Construction of Viral Vectors

According to a particular embodiment, the invention involves the construction and use of viral vectors which enable the above-defined nucleic acids to be transferred and to be expressed in vivo.

More specifically, various adenovirus serotypes, whose structure and properties vary somewhat, were characterized. Of these serotypes, preference is given, within the context of the present invention, to using type 2 or type 5 human adenoviruses (Ad 2 or Ad 5) or adenoviruses of animal origin (see application WO94/26914). Those adenoviruses of animal origin which can be used within the context of the present invention and which may be mentioned are the adenoviruses of canine, bovine, murine (example: Mav1, Beard et al., Virology 75 (1990) 81), ovine, porcine, avian or simian (example: SAV) origin. The adenovirus of animal origin is preferably a canine adenovirus, more preferably a CAV2 adenovirus [Manhattan or A26/61 strain (ATCC VR-800), for example]. Adenoviruses of human or canine, or mixed, origin are preferably used within the context of the invention.

Preferably, the defective adenoviruses of the invention comprise the ITRs, an encapsidation sequence and a nucleic acid according to the invention. Still more preferably, at least the E1 region is non-functional in the genome of the adenoviruses of the invention. The viral gene in question can be rendered non-functional by any technique known to the skilled person, in particular by total deletion, substitution, partial deletion or addition of one or more bases to the gene or genes in question. Modifications of this nature can be obtained in vitro (on the isolated DNA) or in situ, for example, using genetic engineering techniques or else by treating with mutagenic agents. Other regions can also be modified, in particular the E3 region (WO95/02697), the E2 region (WO94/28938), the E4 region (WO94/28152, WO94/12649, WO95/02697, WO96/22378) and the L5 region (WO95/02697). According to a preferred embodiment, the adenovirus according to the invention contains a deletion in the E1 and E4 regions. According to another preferred embodiment, it contains a deletion in the E1 region into which are inserted the E4 region and the nucleic acid of the invention (WO96/13596). In the viruses of the invention, the deletion in the E1 region preferably extends from nucleotide 455 to nucleotide 3329 in the sequence of the Ad5 adenovirus.

The defective recombinant adenoviruses according to the invention can be prepared by any technique known to the skilled person (Levrero et al., Gene 101 (1991) 195, EP 185 573; Graham, EMBO J. 3 (1984) 2917). In particular, they can be prepared by homologous recombination between an adenovirus and a plasmid which is carrying, inter alia, the DNA sequence of interest. The homologous recombination takes place after the said adenovirus and plasmid have been cotransfected into an appropriate cell line. The cell line employed should preferably (i) be transformable by the said elements and (ii) possess the sequences which are able to complement the part of the genome of the defective adenovirus, preferably in an integrated form in order to avoid the risks of recombination. As an example of a cell line, mention may be made of the human embryonic kidney cell line 293 (Graham et al., J. Gen. Virol. 36 (1977) 59), which harbours, in particular, integrated into its genome, the left-hand part of the genome of an Ad5 adenovirus (12%) or of cell lines which are able to complement the E1 and E4 functions, as described, in particular, in the applications with the Nos. WO94/26914, WO95/02697 and WO96/22378.

The adenoviruses which have multiplied are then recovered and purified using standard molecular biological techniques, as illustrated in the examples.

The adenoassociated viruses (AAV) are DNA viruses of relatively small size which integrate in a stable and site-specific manner into the genome of the cells which they infect. They are able to infect a wide spectrum of cells without giving rise to any effect on cell growth, morphology or differentiation. Furthermore, they do not appear to be involved in human pathologies. The genome of the AAVs has been cloned, sequenced and characterized. It comprises approximately 4700 bases and contains, at each end, an inverted repeat region (ITR) of about 145 bases which serves as the origin of replication for the virus. The remainder of the genome is divided into 2 essential regions which carry the encapsidation functions: the left-hand part of the genome, which contains the rep gene, which is involved in viral replication and expression of the viral genes; the right-hand part of the genome, which contains the cap gene, which encodes the capsid proteins of the virus.

The use of vectors derived from AAVs for transferring genes in vitro and in vivo has been described in the literature (see, in particular, WO 91/18088; WO 93/09239; U.S. Pat. No. 4,797,368, U.S. Pat. No. 5,139,941, EP 488 528). These applications describe various AAV-derived constructs in which the rep and/or cap genes are deleted and replaced with a gene of interest, and the use of these constructs for transferring the said gene of interest in vitro (into cells in culture) or in vivo (directly into an organism). The defective recombinant AAVs according to the invention can be prepared by cotransfecting, into a cell line which is infected with a human auxiliary virus (for example an adenovirus), a plasmid containing a nucleic sequence of the invention, which is of interest and which is flanked by two AAV inverted repeat regions (ITR), and a plasmid carrying the AAV encapsidation genes (rep and cap genes). An example of a cell line which can be used is the cell line 293. The recombinant AAVs which are produced are then purified by means of standard techniques.

The construction of recombinant vectors derived from herpesviruses and retroviruses has been amply described in the literature: see, in particular, Breakfield et al., New Biologist 3 (1991) 203; EP 453242, EP 178220, Bernstein et al., Genet. Eng. 7 (1985) 235; McCormick, BioTechnology 3 (1985) 689, etc. In particular, the retroviruses are integrating viruses which selectively infect dividing cells. They therefore constitute vectors of interest for applications relating to cancer. The retrovirus genome essentially comprises two LTRs, an encapsidation sequence and three coding regions (gag, pol and env). In retrovirus-derived recombinant vectors, the gag, pol and env genes are generally deleted, in whole or in part, and replaced with a heterologous nucleic acid sequence of interest. These vectors can be constructed from various types of retrovirus such as, in particular, MoMuLV (murine moloney leukaemia virus; also termed MoMLV), MSV (murine moloney sarcoma virus), HaSV (harvey sarcoma virus); SNV (spleen necrosis virus); RSV (rous sarcoma virus) or else Friend's virus.

In order to construct recombinant retroviruses according to the invention which contain a nucleic acid according to the invention, a plasmid containing, in particular, the LTRs, the encapsidation sequence and the said nucleic acid is constructed and then used to transfect a so-called encapsidation cell line which is able to supply in trans the retroviral functions which are lacking in the plasmid. Generally, the encapsidation cell lines are therefore able to express the gag, pol and env genes. Encapsidation cell lines of this nature have been described in the prior art, particularly the cell line PA317 (U.S. Pat. No. 4,861,719); the cell line PsiCRIP (WO90/02806) and the cell line GP+envAm-12 (WO89/07150). Furthermore, the recombinant retroviruses can contain modifications within the LTRs for suppressing transcriptional activity as well as extensive encapsidation sequences which include a part of the gag gene (Bender et al., J. Virol. 61 (1987) 1639). The recombinant retroviruses which are produced are then purified by means of standard techniques.

In order to implement the present invention, it is very particularly advantageous to use an adenovirus or a defective recombinant retrovirus. This is because these vectors possess properties which are particularly favourable for transferring genes into tumour cells.

3.3. Chemical Vectors

Of the synthetic vectors which have been developed, preference is given, within the context of the invention, to using cationic polymers of the polylysine, (LKLK)n, (LKKL)n (WO95/21931), polyethylen-imine (WO96/02655) and DEAE dextran type or else cationic lipids or lipofectants. They possess the property of condensing the DNA and of promoting its association with the cell membrane. Of these latter, those which may be mentioned are lipopolyamines (lipofectamine and transfectam, WO95/18863 and WO96/17823), various cationic or neutral lipids (DOTMA, DOGS, DOPE, etc.) and also peptides of nuclear origin (WO96/25508). In addition, the concept of receptor-mediated targeted transfection has been developed, which concept takes advantage of the principle of condensing the DNA with the aid of the cationic polymer while directing attachment of the complex to the membrane due to a chemical coupling between the cationic polymer and the ligand of a membrane receptor which is present on the surface of the cell type which it is desired to transfect. Thus, the targeting of the transferrin receptor, the insulin receptor or the asialoglycoprotein receptor of hepatocytes has been described. A composition according to the invention which uses such a chemical vector is prepared by any technique known to the skilled person, generally by simply bringing the different components into contact.

Example 4

The ScFvs Recognize p53

The association of the ScFvs with p53 was verified in an ELISA test.

A myc tag was fused to the ScFvs to enable them to be detected. The ScFvs 421 and 11D3 (D3M), and a control ScFv (anti-CD3), were produced from the periplasms of bacteria which were expressing these different ScFvs.

ELISA plates which are coated with purified p53 are incubated with various dilutions of 11D3 IgG, 421 IgG, a biotinylated anti-p53 polyclonal serum, the 11D3 ScFv, the 421 ScFv and the anti-CD3 ScFv.

The two IgGs are then visualized using a secondary anti-IgG antibody which is coupled to alkaline phosphatase. The biotinylated serum is visualized using extravidin which is coupled to alkaline phosphatase. The ScFvs are visualized using the anti-myc antibody 9E10 and then using an anti-IgG antibody which is coupled to alkaline phosphatase. A colorimetric assay of the alkaline phosphatase activity is depicted in FIG. 4, which shows that the two purified IgGs, the polyclonal serum and the 421 and 11D3 ScFvs recognize p53 while the anti-CD3 ScFv is inactive.

Example 5

The ScFvs are Able to Induce a Supershift of the Wild-type p53

The ability of the ScFvs to activate the DNA-binding function of the wild-type p53 was tested by means of gel retardation experiments.

A DNA duplex representing a specific binding site for p53 was labelled with $^{32}P$ and then incubated with the purified wild-type p53 and various purified antibodies or ScFvS which were produced in bacterial periplasms. The complexes are resolved by means of electrophoresis on an acrylamide gel.

The results which were obtained are depicted in FIG. 5.

The DNA/p53 complex is seen in the "basal" track. The antibodies HR231, pAb421 and 11D3 are able to induce an additional retardation (supershift) and to increase the quantity of DNA/p53 complex.

The 421 and D3M ScFvs are also able to induce a supershift whereas an anti-ras control ScFv (Y28) has no effect. The 421 ScFv, contrary to the D3M ScFv, induces an increase in the quantity of p53/DNA complex.

Example 6

The ScFvs are Able to Restore a DNA-binding Function to a p53 Mutant

In an analogous manner, the ScFvs were tested for their ability to restore the DNA-binding function of the inactive mutant Trp248. The results which were obtained are depicted in FIG. 6.

They demonstrate that the two ScFvs induce the appearance of a retarded band which corresponds to a p53/DNA complex.

Example 7

The ScFvs are Correctly Expressed in Tumour Cells

The expression of the ScFvs was verified by transiently transfecting expression vectors (SV40 promoter) into H1299 tumour cells. More particularly, the nucleic acids were administered in the form of a plasmid vector of the pSV2 type (Example 3) and in the presence of a cationic lipid, i.e. lipofectamine.

The results which were obtained are depicted in FIG. 7. When a Western blot is carried out on a total extract, a major band is seen which is migrating around 30 kD, which corresponds to the expected size and which confirms that the molecules are expressed at significant levels in tumour cells.

Example 8

The ScFvs are Able Partially to Restore the Transactivating Function of the His273 Mutants The ability of these ScFvs to exert an effect, within tumour cells, on the deficient transactivating function of the mutated forms of p53 was measured in the following manner:

Transient transfections were carried out in cell lines H358 or H1299 (both cell lines being deleted for p53) or in the cell line HT29 (harbouring the p53 mutant His273). These transfections introduced expression vectors for the wild-type p53 or the mutants H273 or His175, for the two ScFvs, and a reporter plasmid which contained the CAT (chloramphenicol acetyl transferase) gene under the control of a p53-dependent promoter. The CAT activity which was measured 48 h after transfection reflects the transactivating function of p53.

The results shown in FIG. 8 indicate that, in cell line H358, the two ScFvs are able to effect a significant reactivation of the transcriptional activity of the mutant His273. Identical results were obtained in the cell line H1299.

In a similar manner, the two ScFvs are able, in cell line HT29, to increase the transcriptional activity of the endogenous mutant His273 (FIG. 9).

What is claimed is:

1. A purified antibody comprising the sequence of SEQ ID NO:2 or 4 which is capable of binding to a p53 protein.

2. A composition comprising an antibody according to claim 1.

3. A purified antibody fragment or a fusion protein thereof which comprises the amino acid sequence of SEQ ID NO: 2 or 4, wherein the fragment or a fusion protein thereof is capable of binding a p53 protein.

4. The fragments of claim 3, comprising the amino acid sequence of SEQ ID NO:2.

5. The fragment of claim 3, comprising the amino acid sequence of SEQ ID NO:4.

* * * * *